(12) United States Patent
D'Alise

(10) Patent No.: US 8,277,218 B2
(45) Date of Patent: Oct. 2, 2012

(54) SCREW-TYPE DENTAL IMPLANT

(76) Inventor: David D. D'Alise, Albuquerque, NM (US)

( * ) Notice: Subject to any disclaimer, the term of this patent is extended or adjusted under 35 U.S.C. 154(b) by 989 days.

(21) Appl. No.: 11/255,846

(22) Filed: Oct. 20, 2005

(65) Prior Publication Data

US 2007/0298379 A1    Dec. 27, 2007

(51) Int. Cl.
*A61C 3/02* (2006.01)
(52) U.S. Cl. ........................................................ 433/174
(58) Field of Classification Search .......... 433/172–174, 433/201.1, 202.1, 215, 220, 221
See application file for complete search history.

(56) References Cited

U.S. PATENT DOCUMENTS

| | | | |
|---|---|---|---|
| 2,112,007 A | | 3/1938 | Adams |
| 4,787,848 A | * | 11/1988 | Ross ............................... 433/174 |
| 4,976,739 A | * | 12/1990 | Duthie, Jr. ....................... 606/60 |
| 5,269,685 A | * | 12/1993 | Jorneus et al. ................. 433/174 |
| 5,588,838 A | | 12/1996 | Hansson et al. |
| 5,601,429 A | | 2/1997 | Blacklock |
| 5,727,943 A | | 3/1998 | Beaty et al. |
| 5,816,812 A | * | 10/1998 | Kownacki et al. ............. 433/174 |
| 6,179,615 B1 | | 1/2001 | Blacklock et al. |
| 6,358,050 B1 | * | 3/2002 | Bergstrom et al. ........... 433/173 |
| 6,402,515 B1 | * | 6/2002 | Palti et al. ...................... 433/174 |
| 6,547,564 B1 | | 4/2003 | Hansson |
| 6,655,961 B2 | | 12/2003 | Cottrell |
| 6,672,872 B2 | | 1/2004 | Cottrell |
| 6,679,701 B1 | | 1/2004 | Blacklock |
| 2002/0182567 A1 | * | 12/2002 | Hurson et al. ................. 433/173 |
| 2003/0104337 A1 | * | 6/2003 | Cottrell ......................... 433/173 |
| 2003/0120279 A1 | | 6/2003 | Hansson |
| 2003/0165796 A1 | * | 9/2003 | Carmichael et al. .......... 433/174 |
| 2003/0170591 A1 | * | 9/2003 | Kurer ............................. 433/165 |
| 2004/0063071 A1 | * | 4/2004 | Schroering .................... 433/174 |
| 2004/0142304 A1 | * | 7/2004 | Cottrell ......................... 433/173 |
| 2004/0170947 A1 | | 9/2004 | Milne |
| 2004/0219488 A1 | * | 11/2004 | Choi et al. ..................... 433/173 |
| 2004/0241611 A1 | * | 12/2004 | Amber et al. .................. 433/173 |
| 2005/0037319 A1 | * | 2/2005 | Bulard et al. .................. 433/173 |
| 2005/0266381 A1 | * | 12/2005 | Abarno .......................... 433/173 |
| 2006/0147880 A1 | * | 7/2006 | Krumsiek et al. ............. 433/174 |
| 2006/0199150 A1 | * | 9/2006 | Niznick ......................... 433/173 |
| 2007/0099153 A1 | * | 5/2007 | Fromovich .................... 433/174 |

OTHER PUBLICATIONS

Constrict. (n.d.). Roget's New Millennium™ Thesaurus, First Edition (v 1.3.1). Retrieved Mar. 18, 2008, from Thesaurus.com website: http://thesaurus.reference.com/browse/constrict.*
Blunt. Merriam-Webster Online Dictionary. Retrieved Mar. 18, 2008, from http://www.merriam-webster.com/dictionary/blunt.*
Auger. Merriam-Webster Online Dictionary. Retrieved Mar. 18, 2008, from http://www.merriam-webster.com/dictionary/auger.*

* cited by examiner

*Primary Examiner* — Heidi M Eide
(74) *Attorney, Agent, or Firm* — Todd E. Rinner

(57) ABSTRACT

A dental implant apparatus consisting of an auger-like lower threaded portion that is screwed into the bone. It includes a divergent intermediate collar with mini-threads for engaging the cortical bone, and a tapered abutment for fixed tooth replacement or a ball-like snap attachment to secure removable dentures. The apical end of the device has a tapered portion with a blunt tip that condenses the medullar bone, which in combination with the divergent collar engaging and wedging into the cortical bone, provides a dual stabilization structure that can be immediately loaded or placed in light function by cementing on a temporary crown or bridge or by lightly attaching a removable full or partial denture.

13 Claims, 6 Drawing Sheets

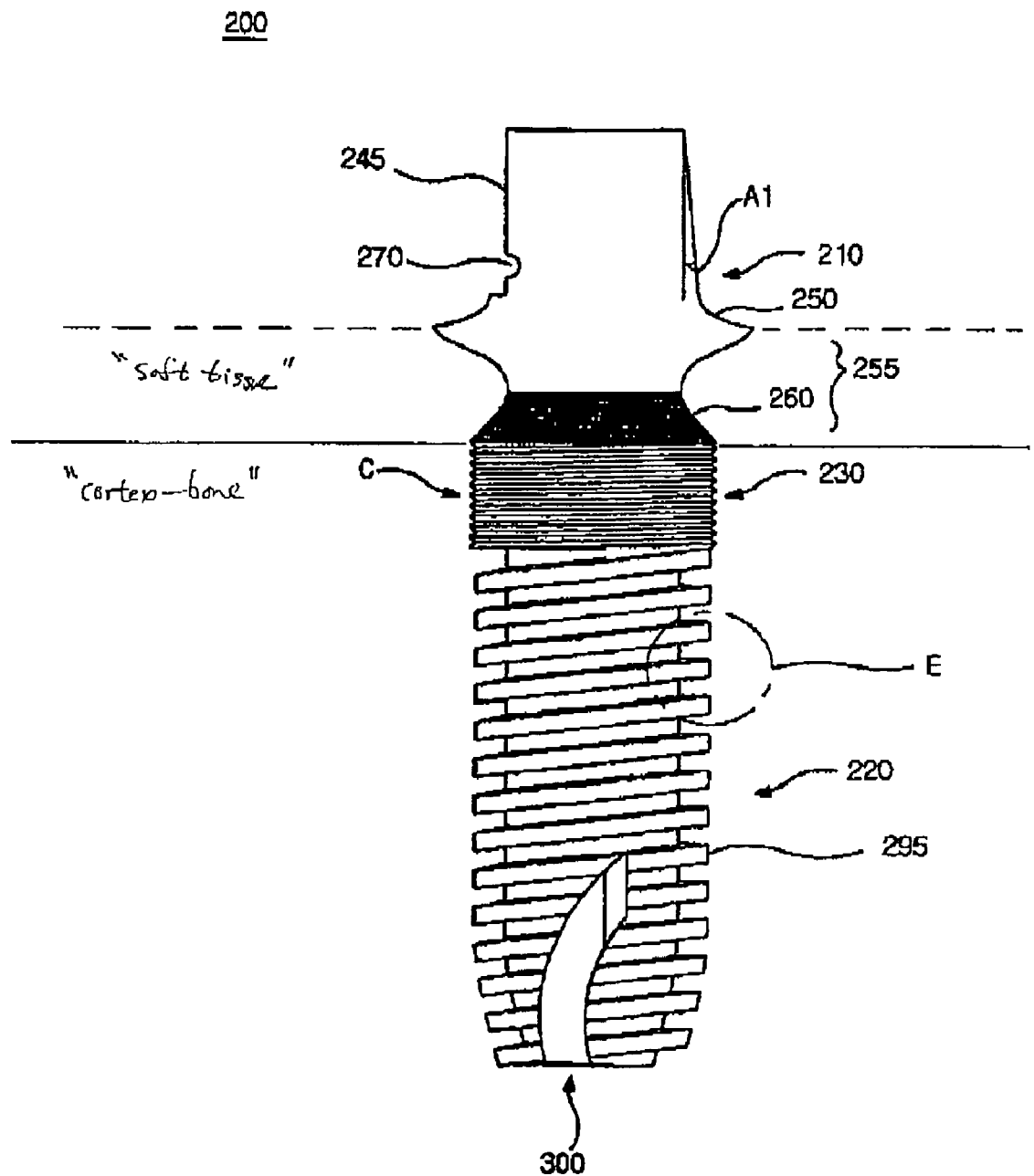

SCREW-TYPE DENTAL IMPLANT

FIELD OF THE INVENTION

This invention relates generally to dental implants, and more specifically to a screw-type dental implant having an improved configuration to more securely affix the implant to the bone structure in a patient's mouth at the time the implant is placed.

BACKGROUND OF THE INVENTION

Dental implants are used in place of missing, or extracted, teeth, whether due to accident or disease, and have the ability to perform the functions of natural teeth. A dental implant is used as an artificial root (support), with an artificial crown (prosthesis) placed on the artificial root after integration with the jawbone. An abutment serves as a spacer between the support and the prosthesis, with the implant serving as the base support for the abutment and final prosthesis in an attempt to restore normal oral function. Alternatively, the prosthesis may be secured directly to the support without utilizing a spacer.

Generally, an implant is surgically placed in a patient's jaw and becomes integrated with the bone. The implant is generally screwed and/or pressed into a hole drilled in the bone and tissue. The surface of the implant has characteristics that aid in the process of osseointegraton. Osseointegration is the process of the bone healing and actually growing up to and locking into the microscopic and macroscopic irregularities of the implant placed in the bone. Typically, once the implant is placed in the bone, full integration of the bone with the jaw bone is required prior to mounting the abutment and prosthesis. The upper end of the implant is typically shaped to receive and secure the abutment in a number of various fashions that are well known in the art, such as that disclosed by Hansson, U.S. Pat. No. 6,547,564.

Implants can be classified according to the location of the implant, such as "intra-osseous," or their shapes, such as "threaded implant." A self-tapping implant is one that can be threaded into a pre-drilled hole in a jawbone without pre-tapping the hole. The apical end portion of the implant taps the hole as the implant is simultaneously rotated and pressed into the hole in the jaw bone.

Various problems exist with the present generation of implant bodies utilized by dentists and surgeons. For one, typical implants require a number of parts. For example, Milne, Pub. No. US 2004/0170947, discusses the common implant comprising a screw-type implant body, an abutment attached to a collar portion of the implant body, and a crown cemented to the abutment. As noted in Choi et al., Pub. No. US 2004/0219488, a multitude of pans can cause slack in the implant structure as a whole. FIG. 1 of Choi et al. depicts a conventional implant comprising numerous separate parts.

Additionally, problems sometimes occur with osseointegration around the collar portion of the implant. For example, Hansson et al., U.S. Pat. No. 5,588,838, discusses the problem stemming from the typically smooth surface of the collar portion in relation to osseointegration of the cortical bone tissue, the strongest part of the bone tissue. Bone tissue sometimes degenerates in the area around a smooth collar portion.

Another problem relates to the period of time required for the bone to bond sufficiently with the implant such that the artificial crown can be mounted and the implant may be used to fully restore oral function. It usually takes approximately 3 to 6 months for the bone to bond sufficiently with the implant to allow mounting the abutment. The need exists for an implant creating a sufficiently strong support structure to allow an abutment and/or prosthesis to be attached to the implant body without waiting for osseointegration to take effect. Thus, an implant structure is needed that creates a higher level of stability by securing itself to the jawbone through its own characteristics immediately, with later osseointegration providing further stability assurance.

Prior methods of surgically placing an implant typically include first cutting a flap in the gum to reveal the jaw bone. The next typical step involves drilling a hole in the jaw bone at the desired implant location, and then inserting the implant and repairing the gun. Because an unnecessarily large portion of the bone is exposed to air, it may cause the bone to recede, sometimes as much as one to two millimeters, which in turn has a negative effect.

SUMMARY OF THE INVENTION

The invention is directed to a screw-type dental implant including a self-tapping, tapered body portion, with externally threaded, auger-like threads. A divergent collar extends from the body portion and is partially threaded with a mini-thread. The implant includes an abutment on top of the collar portion. The abutment has one or more concave grooves extending longitudinally for engaging with a tool for inserting the implant into an opening formed in the bone tissue to receive the implant. The tapered threaded body portion of the implant ends in a blunt tip. The inner diameter of the threads of the tapering portion becomes progressively less, yet the auger-like threads provide a deep thread at the tip of the implant. The preferred embodiment is a one-piece implant, however, an alternative embodiment is a two-piece implant wherein the abutment is screwed into the body portion. In the two-piece implant, the body portion has a cavity and internal threads designed to engage an abutment with a compatible outer shape and external threads. The two-piece embodiment preferably utilizes the threads and a taper to join the body portion and the abutment. Finally, the invention is also directed to a method of placing a dental implant, whether a one-piece or two-piece implant.

DETAILED DESCRIPTION OF THE PREFERRED EMBODIMENT OF THE INVENTION

Figure 1:
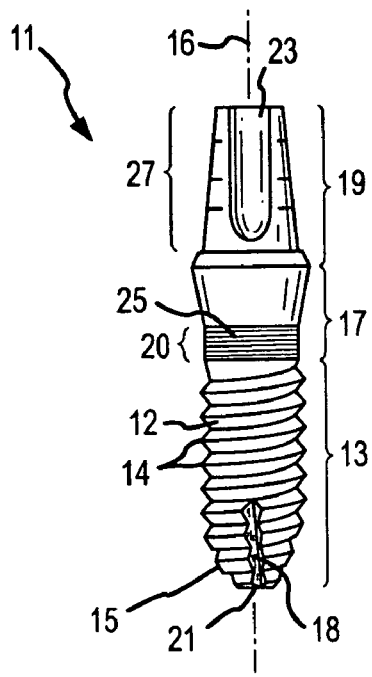
FIG. 1 is a side view of one embodiment of the dental implant wherein the abutment is designed to accept a fixed prosthesis by cementation and has vertical concave grooves for engaging with a compatible driving mechanism.

In a preferred embodiment, the invention is a one-piece screw-type dental implant that includes an externally threaded body portion with auger-like threads that thread into the bone, an intermediate divergent collar, and an abutment for securing a single tooth, multiple teeth, or a denture to the jaw bone. The bottom of the apical end of the body portion preferably has two opposing longitudinal grooves to aid in the implant's self-tapping as it is driven into the bone and also to aid in the removal of bone and blood from the osteotomy hole as the implant is inserted. The tip (apical end) has a blunt, preferably flat, surface, approximately the same diameter as the tip of the pilot drill such that when the implant reaches the bottom of the predrilled hole it will not burrow deeper than the pilot hole. The inner diameter of the auger-like threads on the tapering portion decreases, but the auger-like threads do not taper to a zero-depth thread. The foregoing provides a deep thread (greater thread surface near the tip than typical implants) at the apical end of the implant that pulls the surrounding bone and tissue up and helps the flat tip condense the bone, thus providing stability to the apical end of the implant. The threaded body portion may also have a roughened surface, preferably by grit-blasting, although the surface may also be of any other type well known in the art, such as a machined surface or an acid etched surface or a combination of each. In one embodiment, the surface is roughened by grit-blasting. The divergent collar has mini-threads (also known as micro-threads) on a portion of its exterior, preferably approximately the lower one-third of the collar, for engaging the cortical bone. When finally seated, the collar of the implant extends through the denser cortical bone such that the top level of the bone, with respect to the implant, is just above the mini-threaded portion of the collar. The result is a dual stabilization achieved by condensing the medullar bone at the tip of the implant and wedging and threading the divergent collar into the cortical bone at the collar. The remainder of the collar extends through the over-lying gingiva (gum tissue) to the abutment. The abutment portion extends into the mouth and a crown, or multiple combined crowns, can be cemented to an implant or multiple implants placed with a distance between them approximating that of natural teeth. The abutment also preferably has three concave longitudinal grooves designed to be engaged with a compatible driving tool, for instance, a thumb wrench or driving socket. The grooves also serve to index the attached crown and prevent it from rotating on the abutment when seated. The implant is preferably made of commercially pure titanium alloy. It can also be made of any material having bio-compatible properties similar to titanium. The device preferably has an outside thread diameter ranging from 1.8 to six millimeters. The threaded body portion of the device has a length preferably ranging from six to twenty millimeters.

The preferred method of placing an implant has the advantage of relative simplicity over prior methods. Making an incision and reflecting the gum tissue, as is typical in previous methods, exposes the bone unnecessarily and causes shrinkage of the bone. The preferred method of the invention does not expose the bone unnecessarily and preserves the pointed gum tissue between the teeth, which helps to eliminate an unsightly gap and maintain hygiene by minimizing food impaction during chewing. The typical method generally requires bone grafting at the point where the bone receded. However, the typical method may be used with the apparatus of the invention if bone grafting is desirable.

With respect to the preferred method, first, a pilot drill with a diameter substantially equal to the diameter of the rip of the threaded portion of the implant and the tip of the final osteotomy drill is chilled into the jaw bone to a depth, preferably eight millimeters, less than the predetermined depth of the osteotomy hole using proper alignment relative to remaining teeth or additional implants to be placed in the jaw. Second, an alignment pin is placed in the pilot hole to check the alignment. The alignment pin has a top that duplicates the top of the implant to be placed in the patient. If the alignment is not acceptable, the pilot hole is realigned, redrilled, and/or checked again. Third, a hollow cylindrical soft tissue punch with either a center guide to follow the pilot hole or an inner diameter that allows it to slip over and be guided by the alignment pin is used and rotated through the gum tissue such that the pilot hole is in the center of the hole in the gum tissue where the dental implant is to be placed in the jaw. A center guide will allow the punch to follow the pilot hole. Alternatively, if the inner diameter of the punch is designed to slip over the alignment pin, it will be guided in by following the direction of the alignment pin and the center of the pilot hole. The resulting plug of gum tissue is removed, preferably using a curette or high-speed round drill. Fourth, the pilot drill is then drilled again, but to the predetermined depth of the osteotomy hole establishing the point at which the final osteotomy drill will stop after being drilled into the hole. A final osteotomy drill having a pattern that optimizes the grip of the threads in the bone is used next. The diameter of this final drill is preferably equal to or slightly larger than the inner diameter of the implant threads, selection being made based on the density of the bone. The final drill narrows more at its tip than the dental implant does at its tip in comparison, so there will be more bone available for the tip of the dental implant to grab and condense. Additionally, the final drill has many cutting edges along the length of the drill that enables the drill to cut smoothly through the bone, whereas typical drills have only a couple of cutting edges at the tip. An optional step prior to the final osteotomy drill is to use an intermediate osteotomy drill. The intermediate osteotomy drill has the same features as the final osteotomy drill, except it is slightly narrower. Use of the intermediate osteotomy drill may be advantageous when drilling through particularly dense bone, for instance. The intermediate osteotomy drill would be used as the final drill for one of the lesser diameter implants so that the final osteotomy shape is maintained.

The implant is then threaded with a socket-like wrench, or other compatible driving tool or mechanism, until the implant reaches the predetermined seating depth, which is determined by the person placing the implant, as established by the pilot drill. At that point, a few more turns are then made on the implant, but not necessarily a full rotation of the implant; preferably to a torque of approximately 50-70 N/cm, so that the auger-like thread at the tapering portion of the implant will burrow down slightly further, thus slightly condensing the bone at the tip of the implant and pulling up on the surrounding boney tissue. The depth of the implant should be established so that a portion of the collar is wedged into the outer cortical layer of bone. The rest of the tapered collar penetrates through the hole in the gum tissue above the bone. The abutment of the implant is preferably above the gum tissue. In this preferred manner, a dual stabilization effect is created by the tip condensing the bone around it and the collar wedging into the bone around it that maintains and gives the implant greater biomechanical support and stabilization until final natural healing or osseointegration occurs which, with prior art devices, is usually at a period of three to six months after the implant is placed. The implant's lessened micro-mobility (due to increased biomechanical stabilization) and the close interface of the bone and the implant also reduces the osseointegration time.

With reference to FIG. 1, dental implant 11, which is one piece, includes body portion 13, external threads 14, apical end 15, divergent collar 17, vertical grooves 18 and abutment portion 19. Body portion 13 is the main portion of dental implant 11 that is placed in a jaw bone. Body portion 13 is generally cylindrical in shape and tapers inwardly toward the longitudinal axis 16 of dental implant 1 at apical end 15. Apical end 15 has blunt tip 21 (also referred to as a bull-nose tip), which is preferably a flat tip but may take other forms that are compatible with compressing the bone around tip 21. For example, tip 21 may also be convex in shape. External threads 14 extend along the length of body portion 13 from apical end 15 to a point just before divergent collar 17. Surface 12 of body portion 13 is preferably roughened through the use of grit-blasting, although any of a number of roughening techniques that are well-known in the art may be used, such as various grit-blasting and acid etching methods or combinations of each. Additionally, surface 12 may be machined (generally smooth) in an alternative embodiment (not shown). Surface 12 may have different characteristics (ex. roughened versus smooth) depending on the particular application. For example, a smooth surface may be preferred if the implant will be removed in one to two years (as is the case in some orthodontic anchoring applications) because the smooth surface will be easier to break loose from the bone than a roughened surface. An additional embodiment may utilize a roughened surface for most of the body portion, but the first couple of threads may have a smooth surface to maintain the sharpness of the thread edge lost due to grit-blasting. External threads 14 taper inwardly with body portion 13 as they near apical end 15. Vertical grooves 18 are preferably symmetrically located in body portion 13 and extend from apical end 15 generally along longitudinal axis 16 of dental implant 11 and generally perpendicular to external threads 14. Vertical grooves 18 are effective to self-tap dental implant 11 into the pre-drilled osteotomy hole (shown in FIG. 8) when dental implant 11 is rotated clockwise around its longitudinal axis 16. Vertical grooves 18 also aid in the removal of bone and blood as dental implant 11 is inserted by acting as a relief channel to assist in guiding the blood and bone away from apical end 15, thus reducing hydraulic pressure as dental implant 11 moves downward.

Figure 8:
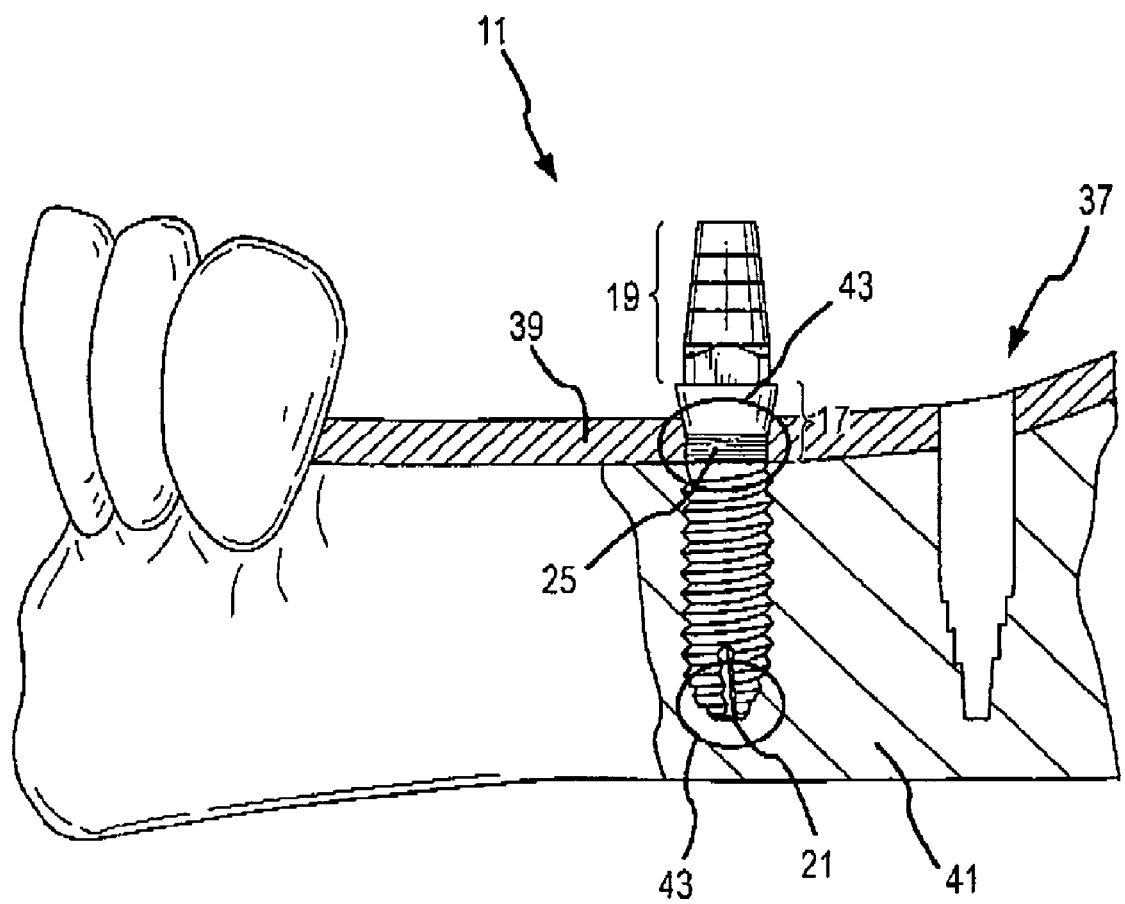
FIG. 8 is a partial cross-sectioned view illustrating the final position of the dental implant in a lower jaw bone after seating the implant such that the medullar bone is condensed below and around the tip and the divergent collar is wedged and threaded into the thin outer layer of cortical bone.

With further reference to FIG. 1, divergent collar 17 extends between body portion 13 and abutment portion 19. Divergent collar 17 preferably comprises uniform section 20 and then increases in diameter as it nears abutment portion 19. Micro-threads 25 are located on the exterior of divergent collar 17 and preferably cover approximately the one-third length of divergent collar 17 nearest body portion 13, which comprises uniform section 20 in the preferred embodiment. When dental implant 11 is properly placed, divergent collar 17 is wedged into the outer, harder cortical bone of the jaw and micro-threads 25 engage the cortical bone, as illustrated in FIG. 8.

Figure 3:
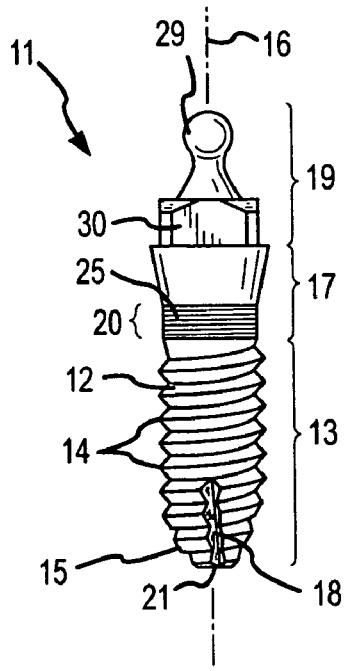
FIG. 3 is a side view of an alternative embodiment of the dental implant wherein the abutment takes the form of male ball attachment designed to functionally interface with a female elastic ring on a prosthesis.

Abutment portion 19, as depicted in FIG. 1, is fitted in a known way for accepting a dental restoration component, such as a crown (not shown). As is known in the art, abutment portion 19 may take the form of tapered portion 27 that ranges, in one embodiment, from approximately three to seven millimeters in length onto which a crown (not shown) is cemented. In an alternative embodiment, as is known in the art and depicted in FIG. 3, abutment portion 19 may take the form of a male ball portion 29 onto which a removable partial or full denture (not shown) is secured to the jaw by an encapsulated ring (not shown) attached to the removable denture.

In FIG. 1, abutment portion 19 also preferably comprises three concave longitudinal grooves 23 designed for engagement by a compatible driving mechanism (not shown), for instance, a socket, open-end wrench, hand-piece adaptor, ratchet, or other tool capable of being used to drive dental implant 11 into the osteotomy hole. The artificial crown (not shown) also engages grooves 23 to prevent rotation of the crown and provide indexed seating during final cementation. Grooves 23 are arranged in a manner so as to index the applied artificial crown such that it will only fit onto abutment portion 19 in a desired orientation. The compatible driving mechanism (not shown), such as a driving socket, may have one or more splines so it may engage any one or more of the three grooves 23.

Figure 2:
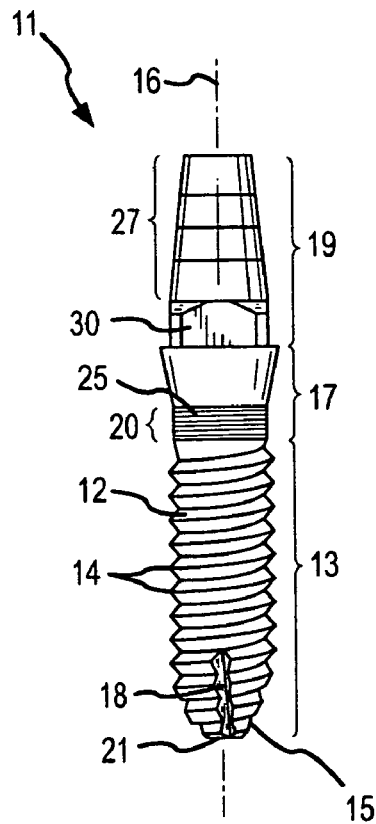
FIG. 2 is a side view of an alternative embodiment of the dental implant wherein the abutment has a square driving section for engaging with a compatible driving mechanism.

FIG. 2 depicts an alternate embodiment of abutment portion 19 wherein multi-surfaced portion 30 is designed to be engaged with a compatible driving mechanism such as a socket-like wrench (not shown). Multi-surfaced portion 30, as depicted, has a rectangular perimeter. For instance, multi-surfaced portion 30 may be a four millimeter by four millimeter section, which is the standard in the industry for sockets, extensions, and other tools. However, it may also encompass a variety of other embodiments well known in the art. Multi-surfaced portion 30 is preferably located at the bottom of and is part of abutment portion 19, adjacent to divergent collar 17. Multi-surfaced portion 30 preferably extends vertically a couple of millimeters along the longitudinal axis 16 of dental implant 11 and also engages an applied crown (not shown), thus acting as an anti-rotation and indexing mechanism for the crown, similar to grooves 23 described with reference to FIG. 1. It is understood that regardless of the particular embodiment, abutment portion 19 must be compatible with a selected crown to properly engage the crown and act as an indexing and anti-rotation element. It is also understood that regardless of the particular embodiment, it is desirable that abutment portion 19 include a mechanism of some type to index and prevent the rotation of a crown, such as the two embodiments described. As previously noted, other embodiments that perform these indexing and anti-rotation functions are well known in the art.

Figure 4:
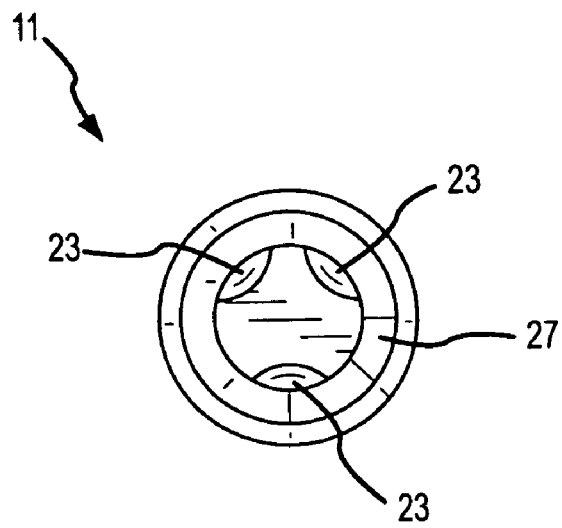
FIG. 4 is a top view of the dental implant of FIG. 1 showing the concave grooves of the abutment designed to engage a compatible driving mechanism.

With reference to FIG. 4, abutment portion 19 (as embodied in FIG. 1) is depicted from a top view. Concave longitudinal grooves 23 are preferably located in a manner so as to index an applied crown. For instance, the angles between grooves 23 may be 135 degrees, 135 degrees, and 90 degrees. A socket-like wrench or other compatible engaging tool (not shown) designed for driving the implant will functionally engage concave longitudinal grooves 23 and enable a surgeon, dentist, or other person placing the implant to rotate the implant and properly position it within the final osteotomy hole (refer to FIG. 8). As noted previously, the compatible engaging tool may have one or more splines so it may engage any one or more of the three grooves 23.

Figure 5:
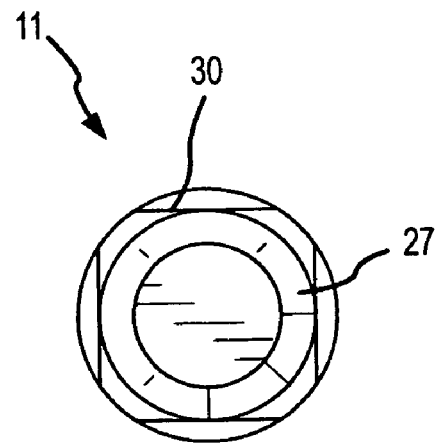
FIG. 5 is a top view of the dental implant of FIG. 2 depicting the square driving section of the abutment for engaging with a compatible driving mechanism.

FIG. 5 further depicts the perimeter of multi-surfaced portion 30 (as embodied in FIG. 2). As noted above, multi-surface portion 30 may take a variety of forms already well-known in the art such as, for instance, a hexagonal perimeter (not shown) for engagement with a hexagonal driving socket with compatible dimensions (not shown).

Figure 6:
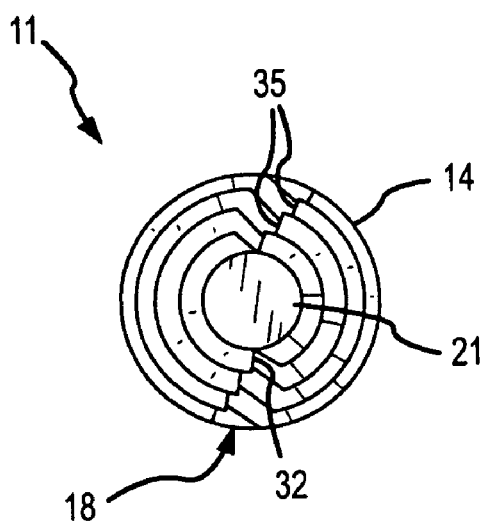
FIG. 6 is an enlarged bottom view of one embodiment of the dental implant showing the auger-like thread pattern and flat tip.

With reference to FIG. 6, which is an enlarged view, apical end 15 of dental implant 11 has blunt tip 21. Lead edge 32 of external threads 14 is depicted and clearly shows the auger-like aspect. Rather than collapsing to a screw point as is typical in other dental implants, external threads 14 begin with abrupt lead edge 32. In a typical implant thread, the outer diameter of the threads reduces to a point such that it becomes equal to the inner diameter of the threads, thus ending the thread pattern in a relatively smooth manner. On dental implant 11, although the outer diameter of external threads 14 reduces as body portion 13 tapers at apical end 15, the outer diameter remains greater than the inner diameter of external threads 14 until the thread pattern reaches lead edge 32. Thus, dental implant 11 has a greater thread surface near tip 21 than typical prior art implants. This greater surface enhances the ability of external threads 14 to engage the bone around tip 21 (see further discussion below).

The effect of such auger-like external threads 14 is that even when dental implant 11 is placed at the predetermined seating depth (i.e. bottom of the final osteotomy hole) and blunt tip 21 is touching the bottom of the hole, a few more turns of dental implant 11, but not necessarily a full rotation of dental implant 11, will cause external threads 14 to engage and move dental implant 11a little further down and pull up the surrounding bone, thus condensing the surrounding bone at apical end 15 of implant 11. Also, this occurs because lead edge 32 is located at blunt tip 21 and will still functionally engage medullar bone 41 in the jaw. Additionally, lead edge 32 assists external threads 14 in engaging the greater portion of bone near the bottom of the osteotomy hole that is created through the use of a final osteotomy drill, which has a greater taper at its tip than the taper of dental implant 11 at its apical end 15 (see discussion below with reference to FIG. 9). Because of the design of lead edge 32, the implant will condense the medullar bone even though blunt tip 21 is at the predetermined searing depth. The end effect is that external threads 14 will continue to pull tip on the surrounding bone, lead edge 32 will continue to burrow, and blunt tip 21 will press down slightly on the bottom of the osteotomy hole and condense medullar bone 41 of the jaw at apical end 15 (refer to FIG. 8), thus, in combination with the divergent micro-threaded collar engaging and wedging into the cortical bone, providing enhanced dial stabilization.

With further reference to FIG. 6, vertical grooves 18 are visible and extend a distance along the length of body portion 13. Vertical grooves 18 form cutting edges 35 that are effective to self-tap the pre-drilled osteotomy hole when dental implant 11 is rotated. Dental implant 11 preferably has two vertical grooves 18, but alternate embodiments may have as few as zero or as many as desired without significantly impairing the function of the implant.

Figure 7:
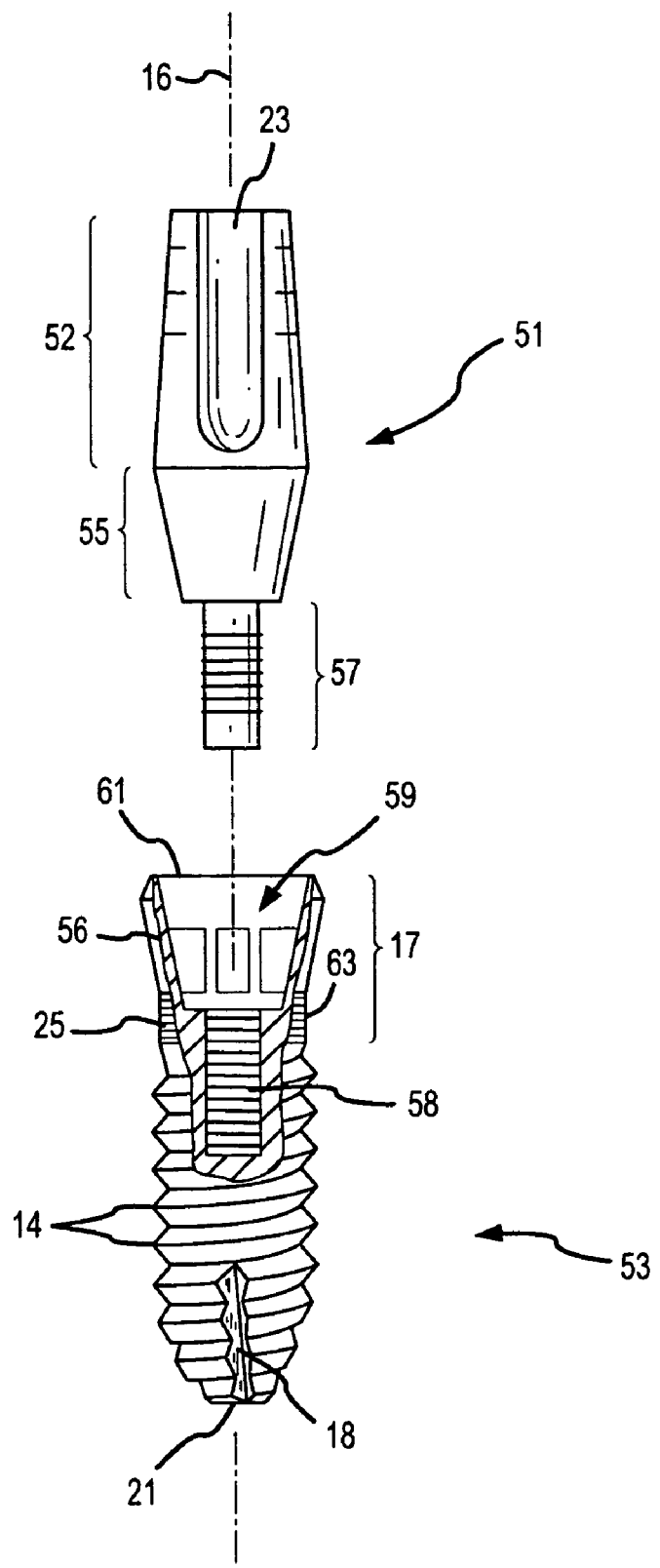
FIG. 7 is a side view of one embodiment of the alternative two-piece implant.

With reference to FIG. 7, an alternative embodiment of the invention is a two-piece implant with a separate abutment 51 and body 53. Body 53, which preferably includes divergent collar 17, micro-threads 25 and the other features previously described with respect to body portion 13 of FIG. 1, has a cavity 59. Cavity 59 has an open end 61 and extends apically into body 53. Cavity 59, which is for receiving and engaging abutment 51, comprises cylindrical section 63 with internal threads 58 and tapered section 56. Abutment 51 has top portion 52, externally threaded apical end 57 and tapered section 55. Tapered section 55 may be retained in cavity 59, for releasably securing abutment 51 to body 53, by engaging externally threaded apical end 57 and internal threads 58. Tapered sections 55 and 56 also aid in securing abutment 51 to body 53 because they frictionally engage due to the uniformity of the taper (acting similar to a Morse taper). Frictionally engaging tapers operate under the principle of basically a cone within a cone. The male portion (tapered section 55 here) and die female section (tapered section 56 here) are uniformly tapered such that when the tapered sections are engaged they come into intimate contact. The friction between tapered sections 55 and 56 aids in keeping body 53 and abutment 51 engaged in a manner similar almost to a cold weld.

The embodiment depicted in FIG. 7 is most useful where immediate loading is not desirable due to bone grafting, augmentation or alteration that would increase the healing time of the bone and/or decreasing the natural stability of the bone structure. Alternatively, this embodiment can be used where the implant is not placed parallel to adjacent teeth or other implants. Offset and angled abutments can be used to align the abutment with other teeth or implants. This embodiment also enables the use of abutments with top portions, similar to top portion 52, of varying heights and angles.

FIG. 8 depicts the typical placement of dental implant 11 in a jaw. The shape of osteotomy hole 37 created by the method previously described is illustrated, as is a second osteotomy hole with dental implant 11 placed in it. When finally seated, divergent collar 17 extends through denser cortical bone 39 such that cortical bone 39 is at a level just above mini-threads 25. As previously discussed, mini-threads 25 add stability by engaging cortical bone 39 of the jaw. The result is dual stabilization areas 43 achieved by condensing the medullar bone 41 at flat tip 21 and wedging divergent collar 17 into cortical bone 39. The remainder of divergent collar 17 extends through the over-lying gingiva (gum tissue) (not shown) to abutment portion 19. Abutment portion 19 extends into the mouth.

Figure 9:
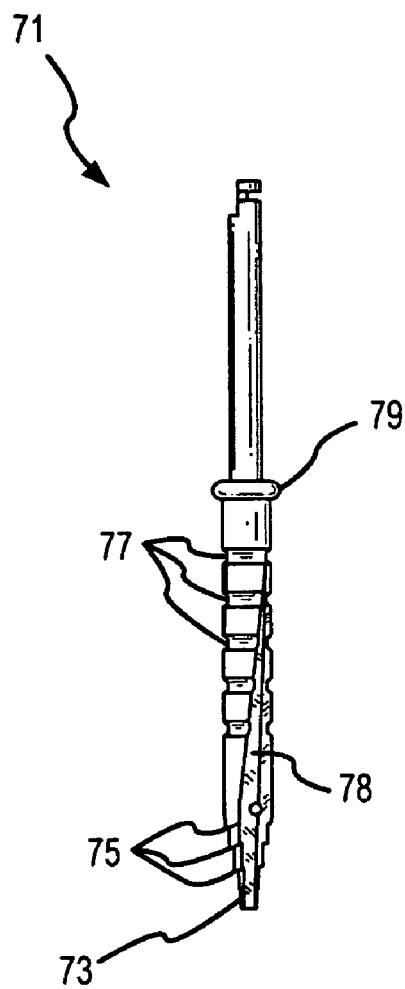
FIG. 9 is a side view of one embodiment of the find osteotomy drill used in the method described herein.

FIG. 9 depicts one embodiment of the final osteotomy drill used in the method described herein for placing a dental implant. Final osteotomy drill 71 has a greater taper at its tip 73 in comparison to the taper of dental implant 11. This greater taper leaves a greater portion of tissue near or at the bottom of the final osteotomy hole (shown in FIG. 8) for external threads 14 of dental implant 11 to engage near the blunt tip 21 of dental implant 11. Final osteotomy drill 71 has numerous taper cutting edges 75 located along the tapering portion of drill 71, as well as numerous body cutting edges 77 located along the length of drill 71. The multitude of cutting edges 75 and 77 enables drill 71 to cut more smoothly through bone than typical drills, which generally have only one or two cutting edges located at their tip. Additionally, final osteotomy drill 71 may be micro-adjusted while drilling by simply applying lateral pressure to the drill, which allows the user to change the alignment of drill 71 without having to back-out drill 71 and restart the drilling. Other advantages of the features of this drill will be apparent to one of skill in the art. Drill 71 also has vertical grooves 78 to aid in the removal of bone, tissue and blood that may accumulate while drilling, as grooves 78 allow such material to pass up the groove. Rubber ring 79 may be adjusted about the length of drill 71 to act as a depth-guide when drilling.

Figure 10:
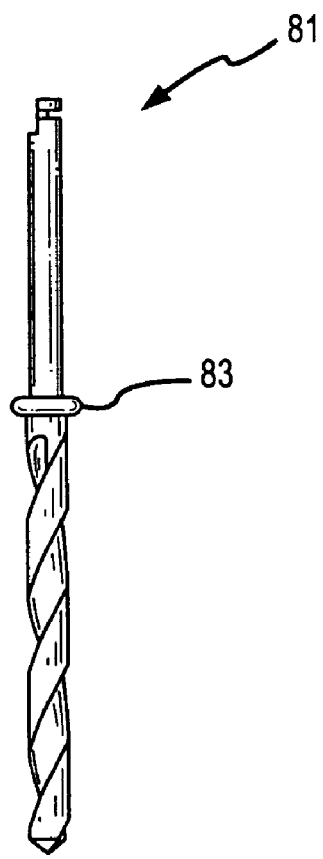
FIG. 10 is a side view of one embodiment of the pilot drill used in the method described herein.

FIG. 10 depicts one embodiment of the pilot drill used in the method described herein for placing a dental implant. Pilot drill 81 is typical of pilot drills used in placing dental implants, and its features and function are well known in the art. Rubber ring 83 may be adjusted about the length of drill 81 to act as a depth-guide when drilling.

Whereas the drawings and accompanying description have shown and described the preferred embodiment of the present invention, it should be apparent to those skilled in the art that various changes may be made in the form of the invention without affecting the scope thereof.

What is claimed is:

1. A generally cylindrical dental implant for placement in a jaw bone comprising a body portion including an apical end and a first threaded outer surface, said implant further comprising a longitudinal axis, said first threaded outer surface extending along said longitudinal axis to said apical end, said implant also comprising a nonthreaded collar continuously diverging as the distance along said longitudinal axis from said apical end increases, said implant also comprising an abutment onto which an item selected from the group of an artificial crown, denture, or prosthesis may be attached, said collar located between said abutment and said body portion at a location such that it will be wedged against or into the jaw bone and extend beyond the jaw bone into gingival tissue when said implant is positioned in the jaw bone as intended, said body portion and said collar not decreasing in diameter as the distance along said longitudinal axis from said apical end to said collar increases.

2. The generally cylindrical dental implant for placement in a jaw bone of claim 1, wherein said first threaded outer surface comprises at least one thread having an outer edge and an outer diameter greater than an inner diameter such that the depth of said at least one thread remains generally constant for the length of said thread, said at least one thread having a leading edge at said apical end of the implant, said leading edge distinguishable from said outer edge.

3. The generally cylindrical dental implant for placement in a jaw bone of claim 1, wherein said apical end comprises a tip adapted to condense the medullar bone.

4. The generally cylindrical dental implant for placement in a jaw bone of claim 1, wherein said apical end comprises a blunt non-cutting tip.

5. The generally cylindrical dental implant for placement in a jaw bone of claim 1, further comprising at least one microthread for interacting with the cortical bone of a jaw when said implant is placed in said jaw, said at least one microthread located below said divergent collar.

6. A dental implant for placement in a jaw bone, comprising a body portion, an abutment, and a divergent collar extending between said body portion and said abutment, said body portion having at least one external thread and an apical end, said apical end comprising a blunt tip, said at least one external thread beginning at said apical end and extending along said body portion such that a portion of said blunt tip extends a small distance beyond said beginning of said at least one external thread, said divergent collar having a first end interfacing with said body portion and a second end interfacing with said abutment.

7. The dental implant for placement in a jaw bone of claim 6, wherein said blunt tip is adapted to condense the medullar bone by said at least one external thread at said apical end pulling up on said medullar bone.

8. A method of placing a dental implant having a body portion, including exterior threads and a tip, and a divergent collar, comprising the steps of:
   (a) drilling an osteotomy hole in a jaw bone of a patient;
   (b) threading said dental implant into said osteotomy hole;
   (c) causing said dental implant to condense said bone around said tip of said dental implant; and
   (d) causing said divergent collar to wedge into said bone around said divergent collar.

9. A dental implant for placement in a jaw bone comprising a body portion having at least one external thread and an apical end including a blunt non-cutting tip, said at least one external thread beginning at or near said apical end and adapted to pull up on and condense the bone around said tip.

10. The dental implant for placement in a jaw bone of claim 9, wherein said at least one external thread comprises an auger thread.

11. The dental implant for placement in a jaw bone of claim 9, wherein said at least one external thread comprises an outer edge and an outer diameter greater than an inner diameter for the length of the at least one thread such that the depth of said at least one external thread remains generally constant for the length of said at least one external thread, said at least one external thread having a leading edge at said apical end distinguishable from said outer edge.

12. The dental implant for placement in a jaw bone of claim 9, wherein said blunt tip extends a small distance beyond said at least one external thread.

13. The dental implant for placement in a jaw bone of claim 9, further comprising a collar that diverges as the distance along a longitudinal axis from said apical end to said collar increases.

* * * * *